United States Patent [19]

Leonard

[11] Patent Number: 5,409,710
[45] Date of Patent: Apr. 25, 1995

[54] FOAM CELL DRUG DELIVERY
[75] Inventor: Robert J. Leonard, Lynnfield, Mass.
[73] Assignee: Endocon, Inc., South Walpole, Mass.
[21] Appl. No.: 49,943
[22] Filed: Apr. 20, 1993
[51] Int. Cl.⁶ .......................... A61K 9/14; A61K 9/127
[52] U.S. Cl. .................................... 424/489; 424/450; 424/93.1; 435/240.1
[58] Field of Search ...................... 424/450, 93 R, 489; 428/402.2; 436/829; 435/240

[56] References Cited
U.S. PATENT DOCUMENTS

| | | | |
|---|---|---|---|
| 4,021,280 | 5/1977 | Rinde | 156/80 |
| 4,652,449 | 3/1987 | Ropars et al. | 424/101 |
| 5,004,681 | 4/1991 | Boyse et al. | 435/2 |
| 5,061,620 | 10/1991 | Tsukamoto et al. | 435/7.21 |
| 5,084,441 | 1/1992 | Shaw et al. | 514/2 |
| 5,192,264 | 3/1993 | Fossel | 604/4 |
| 5,288,711 | 2/1994 | Mitchell | 514/56 |

FOREIGN PATENT DOCUMENTS

WO92/21330 12/1992 WIPO .

OTHER PUBLICATIONS

Alan M. Fogelman et al., Proc. Natl. Acad. Sci. USA, vol. 77, No. 4, pp. 2214–2218, Apr. 1980, "Malondialdehyde alteration of low density lipoproteins leads to cholesteryl ester accumulation in human monocyte–macrophages".
Michael S. Brown et al., Nature vol. 316, Aug. 1985, 680–681 "Scavenger cell receptor shared".
Goldstein et al., Proc. Natl. Acad. Sci. USA 76:333–337 (1979) "Binding Site on Macrophages That Mediates Uptake and Degradation of Acetylated Low Density Lipoprotein, Producing Massive Cholesterol Deposition".
Steinbrecher et al., Proc. Natl. Acad. Sci. USA 81:3883–3887 (1984) "Modification of Low Density Lipoprotein by Endothelial Cells Involves Lipid Peroxidation and Degradation of Low Density Lipoprotein Phospholipids".
Henriksen et al., Proc. Natl. Acad. Sci. USA 78:6449–6503 (1981) "Enhanced Macrophage Degradation of Low Density Lipoprotein Previously Incubated with Cultured Endothelial Cells: Recognition by Receptors for Acetylated Low Density Lipoproteins".
Kodama et al., Nature 343:531–535 (1990) "Type I Macrophage Scavenger Receptor Contains a-Helical and Collagen-Like Coiled Coils".
Stanton, L., et al., 267(31):22446–22451 (1992) "A Macrophage Fc Receptor for IgG Is Also a Receptor for Oxidized Low Density Lipoprotein".
Nicolas, J., et al.; Annals of Tropical Med. and Parasitology 83(4):325–336 (1990) "Acetylated Low-Density Lipoprotein As A Vehicle For Antiinfectious Drugs; Preparation and Antileishmanial Activity of Ac-LDL Containing Ketoconazole-oleate".
Steinberg, D., et al., NEJM 320(14):915–923 (1989) "Modifications of Low-Density Lipoprotein That Increase its Atherogenicity".
Racoosin, Ester, et al., Journal of Cell Science, vol. 102, 867–880 (1992) "M-CSF-Induced Macropinocytosis Increases Solute Endocytosis But Not Receptor-Mediated Endoytosis In Mouse Macrophages".
Moulton, K., et al., PNAS USA 89:8102–8106 (1992) "Regulated Expression of the Human Acetylated Low Density Lipoprotein Receptor Gene and Isolation of Promoter Sequences".

(List continued on next page.)

Primary Examiner—Gollamudi S. Kishore
Attorney, Agent, or Firm—Wolf, Greenfield & Sacks

[57] ABSTRACT

Methods and pharmaceutical compositions for delivering a clinically relevant agent to a mammalian recipient in vivo are provided. The methods involve forming a foam cell from an isolated foam cell precursor in vitro, incorporating an agent into the foam cell, and administering the foam cell containing the agent to the mammalian recipient. In a preferred embodiment, the foam cell precursors are isolated from a human recipient, treated, and returned to the patient in the form of a foam cell containing a therapeutically effective amount of the agent.

15 Claims, 2 Drawing Sheets

OTHER PUBLICATIONS

Magnani, M., et al., PNAS USA 89:6477–6481 (1992) "Targeting Antiretroviral nucleoside analogues in Phosphorylated Form to Macrophages: In vitro and in vivo Studies".

Andreesen, R., et al., Cancer Detect. Prev. 15(5):413–421 (1991) "A New Approach to Adoptive Immunotherapy of Cancer Using Tumorcytotoxic Macrophages Grown from Peripheral Blood Monocytes".

Roma, P., et al., J. Lipid Res. 33:819–829 (1992) "Defective Catabolism of Oxidized LDL by J774 Murine Macrophages".

Basu, et al., (PNAS USA 73:3178–3182 (1976) "Degradation of Cationized Low Density Lipoprotein and Regulation of Cholesterol Metabolism in Homozygous Familial Hypercholesterolemia Fibroblasts".

Steinbrecher, U. P., et al., Arteriosclerosis 7(2):135–143 (1987) "Decrease in Reactive Amino Groups during Oxidation or Endothelial Cell Modification of LDL".

Steinbrecher, U. P., J. Biol. Chem. 262:3603–3608 (1987) "Oxidation of Human Low Density Lipoprotein Results in Derivatization of Lysine Residues of Apolipoprotein B by Lipid Peroxide Decomposition Products".

Brown, M. S. and Goldstein, J. L. Annu. Rev. Biochem. 52:223–261 (1983) "Lipoprotein Metabolism In the Macrophage: Implications for Cholesterol Deposition in Atherosclerosis1".

Koo, C., et al., J. Biol. Chem. 261:11194–11201 (1986) "Uptake of Canine $\beta$-Very Low Density Lipoproteins by Mouse Peritoneal Macrophages is Mediated by a Low Density Lipoprotein Receptor".

Charman, W. and Stella, W., "Lymphatic Transport of Drugs", CRC Press, 1992, pp. 115, 193, 256, 273–274.

Garzon-Aburbeh, A., et al., J. Med. Chem. 26:1200–1203 (1983) "1,3-Dipalmitoylglycerol Ester of Chlorambucil as a Lymphotropic, Orally Administrable Antineoplastic Agent".

Steinbrecher, U. P., et al. J. Biol. Chem. 264:15216–15223 (1989) "Recognition of Oxidized Low Density Lipoprotein by the Scavenger Receptor of Macrophages Results from Derivatization of Apolipoprotein B by Products of Fatty Acid Peroxidation".

Bilheimer, D. W., et al., Biochim. Biophys. Acta. 250:212–221 (1972) "The Metabolism of Very Low Density Lipoprotein Proteins I. Preliminary In vitro and in vivo Observations".

Palsson et al., BioTechnology, vol. 11, 368–372 (1993), "Expansion of Human Bone Marrow Progenitor Cells in a High Cell Density Continuous Perfusion Systemitor".

Hamilton, "Molecular Mechanisms in the Activation of Mononuclear Phagocytes", Chapter 9, 213–252.

Anderson, F. D. et al., Pharmaceutical Research, vol. 10, No. 3, 369–380 (1993) "Tissue Response to Bioerodible Subcutaneous Drug Implants: A Possible Determinant of Drug Absorption Kinetics".

Kotake, Hidetoshi, Biochimica et Biophysica Acta, vol. 1138, 327–333 (1992), "T Lymphocytes Increase the Synthesis of Esterified Cholesterol In Human Monocyte-Derived Macrophages by Activation of the Scavenger Pathway".

FOAM CELL DRUG DELIVERY

FIELD OF THE INVENTION

This invention relates to methods and pharmaceutical compositions for delivering a clinically relevant agent to a mammalian recipient. The methods include incorporating the agent into a foam cell for administration to the recipient.

BACKGROUND OF THE INVENTION

An early event in the development of atherosclerotic lesions is the accumulation of lipid by subendothelial macrophages known as "foam cells". The foam cells are characterized by an increased number of lipoprotein receptors and/or an enhanced ability to internalize lipoproteins and/or lipids. To inhibit artheroschlerotic lesion formation, research has been directed to the identification of receptors which mediate foam cell generation in vivo. To this end, various forms of modified low density lipoproteins ("LDLs"), including acetylated LDL ("acLDL") (Goldstein et al., *Proc. Natl. Acad. Sci. USA* 76:333-337 (1979)) and oxidized LDL ("oxLDL") (Steinbrecher et al., *Proc. Natl. Acad. Sci. USA* 81:3883-3887 (1984); and Henriksen et al., *Proc. Natl. Acad. Sci. USA* 78:6499-6503 (1981)) have been prepared and tested for their ability to increase LDL particle uptake by macrophages in vitro.

A macrophage receptor which mediates acLDL uptake has been purified and the gene encoding this protein (also known as the "scavenger receptor") has been cloned (Kodama et al., *Nature* 343:531-535 (1990)). In contrast to the LDL receptor (which does not recognize acLDL), expression of the scavenger receptor is not down-regulated by high levels of intracellular cholesterol (Goldstein, J. L., et al., *Proc. Natl. Acad. Sci. USA* 76:333-337 (1979)).

In addition to acLDL, oxidized LDL ("oxLDL") has been shown to selectively bind to the acLDL receptor (Henriksen et al., *Proc. Natl. Acad. Sci. USA* 78:6499-6503 (1981)). Since acLDL has not been detected in situ or in vivo, oxLDL appears to be the physiologic ligand for this receptor (Stanton, L., et al., supra.). Thus, the binding of oxLDL to the acLDL receptor appears to contribute to macrophage lipid loading in vivo.

A recent study of the uptake of oxLDL by macrophages and by transfected 293 cells expressing the mouse acLDL receptor, suggests that an additional receptor ("FcgammaRII-B2"), known to mediate immune complex uptake via recognition of the Fc region of IgG, also serves as an additional high affinity receptor for oxLDL. Whether lipoprotein internalization via the Fc receptor leads to foam cell formation has not been addressed in the literature.

In view of the high specificity of the above-identified receptors, various attempts have been made in the prior art to utilize these receptors for delivering a drug to a macrophage in vivo. (See e.g., U.S. Pat. No. 5,192,264; Nicolas, J., et al., *Annals of Tropical Med. and Parasitology* 83(4):325-336 (1990)). In general, these therapeutic methods have in common the administration of a lipophilic drug to a patient's bloodstream, followed by internalization of the drug by the macrophage in vivo.

SUMMARY OF THE INVENTION

In contrast to the prior art, the instant invention provides a novel method for delivering a therapeutically effective dose of a clinically relevant agent to a mammalian recipient. According to one aspect of the invention, a method for delivering an agent to the mammalian recipient is provided. The method involves forming a foam cell from an isolated foam cell precursor, incorporating an agent into the foam cell, and administering the foam cell containing the agent to the mammalian recipient. In a preferred embodiment, the foam cell precursors are isolated from a human patient, treated, and returned to the patient in the form of a foam cell containing a therapeutically effective amount of the agent.

Foam cell precursors include stem cells and stem cell derivatives, such as promonocytes, monocytes and macrophages. These can be isolated from, for example, whole or processed blood, plasma, serum or bone marrow. These precursors express or are stimulated to express receptors that are capable of specifically recognizing and binding a foam cell stimulating ligand. Contacting the foam cell precursor with a foam cell stimulating ligand results in foam cell formation. Exemplary stimulating ligands include modified low density lipoproteins (LDL) such as oxidized or acetylated LDL.

The foam cell is characterized by its enhanced ability to internalize lipid or lipoprotein in comparison with the same cell type which has not been exposed to the stimulating ligand. In a preferred embodiment, the foam cell precursor is a macrophage that naturally expresses or is induced to express a plurality of acetyl-LDL receptors. Binding of oxidized LDL to the acetyl-LDL receptor results in enhanced lipid and/or lipoprotein internalization. As described above, other receptors (e.g. the receptors for LDL and Fc) have been implicated in the transformation of a foam cell precursor to a foam cell.

The clinically relevant agent preferably is in a lipophilic form for incorporation into the foam cell. By "lipophilic form," it is meant that the agent is lipophilic or is coupled to or associated with a lipophilic carrier. As used herein, the terms "clinically relevant agent" or "agent" embrace therapeutic drugs and diagnostic agents, in their natural and/or derivatized form (e.g., associated with a lipophilic carrier). The association of an agent with a lipophilic carrier can take a variety of forms, including that of a prodrug in which the agent is covalently attached to a lipophilic carrier. The agent can also be suspended in a lipophilic emulsion or contained within a liposome. Such emulsions and liposomes are prepared according to procedures known to one of ordinary skill in the art without the need for undue experimentation.

According to one preferred embodiment, the agent is a prodrug containing a therapeutic agent covalently coupled to a modified LDL. The modified LDL portion of the prodrug serves: (1) as a stimulating ligand to stimulate formation of a foam cell from a foam cell precursor (e.g., macrophage) and (2) as a lipophilic carrier for conveying the agent into the foam cell. Contacting the prodrug with the foam cell precursor results in the simultaneous formation of the foam cell and incorporation of agent therein. Alternate methods of simultaneously forming the foam cell and incorporating an agent therein are also provided.

The foam cell containing the agent is administered to the mammalian recipient according to methods known in the art. In a preferred embodiment, the agent is delivered to the patient's lymphatic system by injecting the foam cell into a lymph node of the patient. In a most preferred embodiment, the foam cell is administered to the lymph node in the presence of oxidized LDL. It is believed that the oxidized LDL reduces the motility of the foam cell, thereby increasing the period of time that the foam cell remains within the lymph node.

According to another aspect of the invention, a pharmaceutical preparation for delivering an agent to a mammalian recipient is provided. The preparation includes a pharmaceutically acceptable carrier and a plurality of foam cells containing the agent. The preparation contains an amount of foam cells sufficient to deliver a therapeutically effective dose of agent to the mammalian recipient.

These and other aspects of the invention as well as various advantages and utilities will be more apparent with reference to the detailed description below.

DETAILED DESCRIPTION OF THE INVENTION

Figure 1:
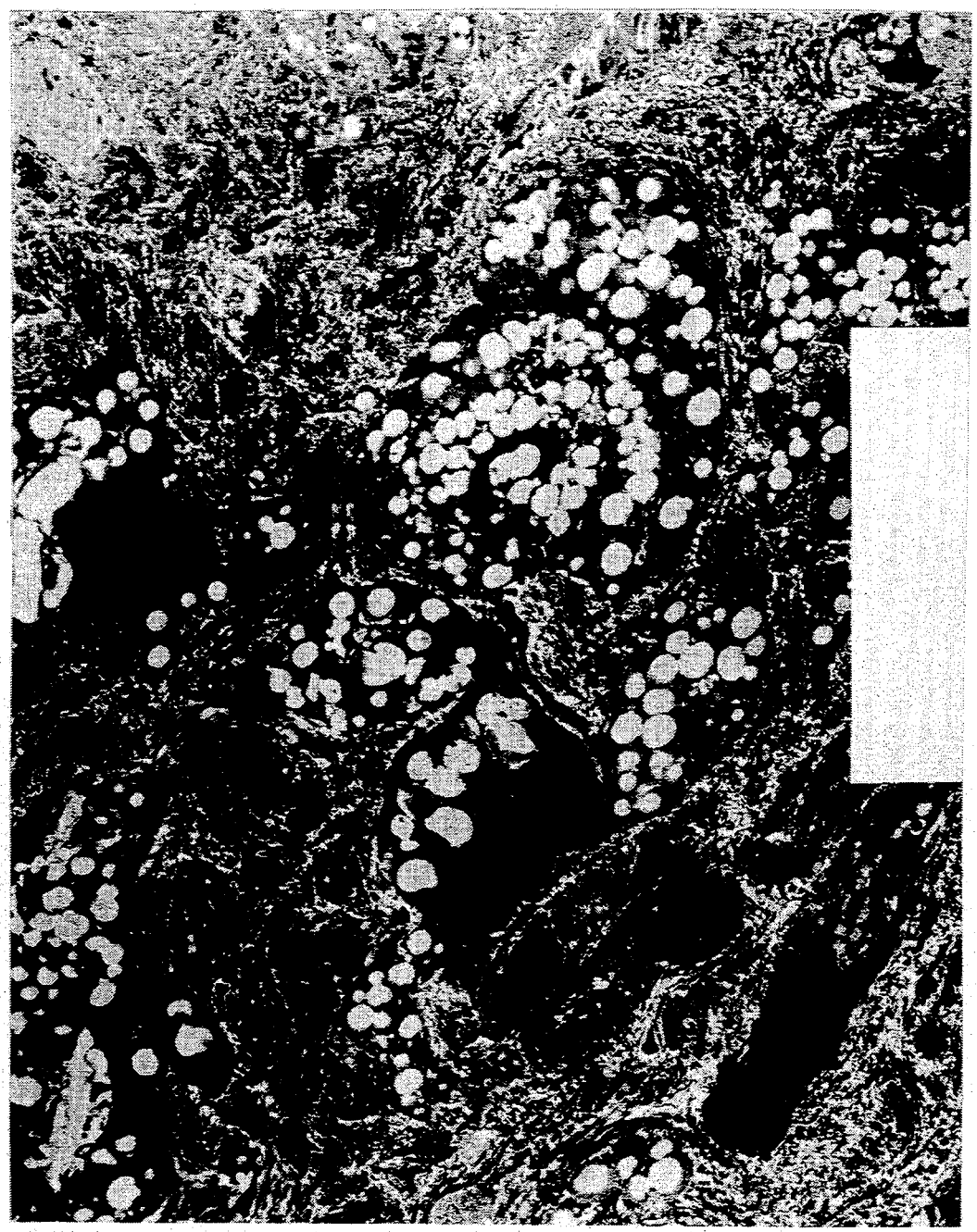
FIG. 1 is copy of a photograph taken at 5,700x magnification showing foam cells lying between collagen bundles and tissue at the site of implantation of a drug-delivering capsule (at six months post-implantation)

One method for forming a foam cell involves contacting an isolated foam cell precursor with a foam cell stimulating ligand. In vivo, foam cells typically arise from circulating monocytes that have become deposited beneath the vascular endothelium, although the derivation of foam cells from smooth-muscle cells has also been reported. (Steinberg, D., et al., *NEJM* 320(14):915–923 (1989). Thus, in vitro, the preferred foam cell precursors include isolated stem cells and stem cell derivatives, such as monocytes and macrophages, as well as smooth muscle cells. Isolated stem cells are prepared according to U.S. Pat. Nos. 5,004,681 and 5,061,620, the contents of which patents are incorporated herein by reference. Stem cell derivatives are prepared by contacting the isolated stem cells with differentiation agents under conditions known to induce differentiation of the stem cell to the desired cell type. For example, contacting a monocyte with macrophage-colony stimulating factor (M-CSF) results in differentiation of the monocyte into a macrophage. The extent of differentiation into a particular cell type is determined by observing the presence or absence of cell specific markers on the cell surface (*Basic and Clinical Immunology*, Seventh Edition, Appleton & Lange, Norwalk, Conn. (1991)). The acetyl LDL receptor is an exemplary marker for the study of macrophage differentiation because of its preferential expression in macrophages (Moulton, K., et al., supra.).

In general, the monocytes are isolated from peripheral blood or lymph fluid; however, monocytes can also be obtained from placental tissue. The preferred foam cell precursors are monocytes that have been isolated from the mammalian recipient.

Various methods are available for preparing mononuclear cells (monocytes) from human donors, see e.g., the preparation of mononuclear cells by Ficoll-Paque sedimentation described in Magnani, M., et al., *PNAS USA* 89:6477–6481 (1992). Following removal of nonadherent cells, the proportion of monocyte-macrophages (M/M) maintained in culture is determined by, for example, nonspecific esterase staining Leu-M3 positivity (Magnani, M., et al., supra.) and/or by acLDL receptor quantitation. In general, the M/M cells are maintained and cultured in fresh RPMI complete medium (Magnani, M., et al., supra.).

Alternatively, the monocytes are isolated from whole blood by cytopheresis and cultured with autologous serum as reported in Andreesen, R., et al., *Cancer Detect. Prev.* 15(5):413–421 (1991). Prior to harvesting the cells, recombinant human interferon gamma (IFN gamma) is added at approximately 200 IU/ml and the monocyte-derived macrophages are purified by counter-current elutriation (Andreesen, R., et al., supra.).

LDL is made up of phospholipids and a large core protein of 514 kD, protein B-100. Low density lipoprotein (LDL) receptors located on the macrophage membrane bind the protein component of LDL (protein B-100) and internalize the LDL particles. Once inside the cell, the LDL is broken down and the receptor is returned to the cell membrane. The cholesterol originating from the LDL or otherwise internalized is incorporated into the cell membrane or stored in the cell in esterified form. The accumulation of cholesterol in the cell down regulates LDL receptor expression but does not appreciably affect expression of the acLDL receptor (See Moulton, K., et al., *PNAS USA* 89:8102–8106 (1992) and references cited therein). Accordingly, it is generally believed that the acLDL receptor, plays a key role in foam cell generation in vivo.

The specific physiclogic regulators of acLDL receptor gene expression are not well defined, but may include macrophage colony-stimulating factor (M-CSF) and platelet secretory products (see Moulton, K., et al., supra., and references cited therein). Moulton et al., report that in THP-1 cells (a human monocytic leukemia cell line), treatment with 12-myristate 13-acetate (TPA, for 12-O-tetradecanoylphorbol 13-acetate), promotes differentiation of macrophage-like cells and induces expression of the acLDL receptor. Accordingly, the instant invention embraces a preparation of macrophages characterized in having enhanced expression of the acLDL receptor.

The foam cells are prepared by culturing isolated monocytes from the designated human recipient under conditions to generate macrophages. Such conditions are well known to those of ordinary skill in the art. Optionally, the monocytes are also contacted with an expression inducer, such as TPA, to induce expression of acLDL receptors. Following differentiation and expression of the acLDL receptor, the macrophage can be contacted with a modified LDL (e.g., acLDL or oxLDL) which binds to the acLDL receptor and induces transformation of the macrophage into a foam cell.

Figure 2:
FIG. 2 is a copy of a photograph taken at 5,700x magnification showing foam cells lying between collagen bundles and tissue at the site of implantation of a drug-delivering capsule (at thirteen months post-implantation).

As used herein, the term "foam cell" refers to a cell which has been stimulated by a foam cell stimulating ligand to have an enhanced ability to take up lipoproteins in comparison with a cell which has not been so stimulated. Enhanced uptake may be measured according to conventional procedures, some of which are described below. Foam cells can be identified morphologically as well. Once they have taken up lipid, they appear larger than a normal macrophage, but smaller than a giant cell. They appear to lack interdigitation pseudopodia. They are lipid-laden, loaded with droplets of lipid to the apparent visual exclusion of reticulum and organelles. The droplets are approximately one tenth the size of the nucleus (see FIGS. 1 and 2).

Transformation of a macrophage into a foam cell in vitro is accomplished by contacting the macrophage with a foam cell stimulating ligand. In a preferred embodiment the ligand is an agonist of a receptor which specifically recognizes a modified LDL. Exemplary receptors include the receptors for acetyl LDL and oxLDL (Steinberg, et al. supra.) and for Fc (Stanton, L., et al., supra.). Exemplary stimulating ligands for these receptors are described below.

The term "modified LDL" refers to a low density lipoprotein (LDL) that: (1) binds to a modified LDL receptor and (2) initiates transformation of a foam cell precursor into a foam cell. The modified LDLs are prepared from commercially obtained LDL (Bionetics Research Institute, Rockville, Md.) or from LDL isolated from human plasma (Roma, P., et al., *J. Lipid Res.* 33:819–829 (1992). Exemplary modified LDLs include acetyl LDL (acLDL) and oxidized LDL (oxLDL). Acetyl LDL is prepared according to the method of Basu, et al. (*PNAS USA* 73:3178–3182 (1976), see also Roma, P. et al., supra.). Oxidized LDL is prepared by oxidizing LDL either chemically, for example, by incubating LDL at 37° C. for 24 hours, at 0.2 mg protein/ml in PBS with 20 uM CuSO4 (Roma, P., et al., supra.) or via a cell-mediated process, e.g., by incubating LDL in the presence of endothelial cells at 37° C. for 24 hours, at a concentration of 0.07–0.1 mg protein/ml, in serum-free medium containing 12 uM CuSO4 (see Roma, P., et al., supra. and references cited therein, and the Examples).

In addition to endothelial cells for effecting cellular LDL- based oxidation, Steinberg, D., et al. report that smooth-muscle cells or macrophages can also be used to biologically oxidize LDL, e.g., by incubating the cells at 10 ug to 100 ug of LDL protein per ml in protein-free Ham's F-10 medium for 20–24 hours at 37° C. Steinberg further reports that a modified procedure (including 5 uM copper ion in the absence of cells) results in chemically oxidized LDL. Thus, the in vivo oxidation of LDLs can be mimicked in vitro by incubating LDL in a serum-free medium in the presence of a sufficiently high concentration of copper or iron (Steinberg, D., et al., *NEJM* 320(14):915–924 (1989) and references contained therein). The oxidation reactions are inhibited by antioxidants, such as butylated hydroxytoluene or vitamin E, and reportedly are dependent on the presence of low concentrations of copper or iron. Accordingly, metal chelators, such as EDTA, inhibit the oxidative modification of LDL. Additional methods for preparing oxidized LDL are disclosed in U.S. Pat. No. 5,192,264, the contents of which patent are incorporated herein by reference.

U.S. Pat. No. 5,192,264 discloses methods for enzymatically oxidizing lipoproteins such as LDL, (e.g. using horseradish peroxidase and hydrogen peroxide). In contrast to the above-referenced literature which establishes the ability of oxLDL to stimulate foam cell formation, U.S. Pat. No. 5,192,264 teaches that administration of oxidized lipoproteins to cells is cytotoxic. To date, there does not appear to be a concensus in regard to the cytotoxity of oxLDL. However, it is generally believed that the peroxidation of polyunsaturated fatty acids in LDL lipids is a common initiating step for both cellular and non-cellular LDL oxidation. Further oxidation leads to extensive fragmentation of the fatty acid chains. Thereafter, the attachment of at least some of these fatty fragments to apoprotein B changes the size and electrophoretic motility of apoprotein B. Accordingly, the extent of lipoprotein oxidation is determined by evaluation of apoB fragmentation using agarose gel electrophoresis in accordance with methods known to one of ordinary skill in the art.

The fragments of the oxidized fatty acids attach covalently to the lysine epsilon amino groups of apoprotein B (Steinbrecher, U. P., et al., *Arteriosclerosis* 1:135–143 (1987); Steinbrecher, U. P., *J. Biol. Chem.* 262:3603–3608 (1987)). Accordingly, it has been suggested that one reason the acLDL receptor recognizes both acLDL and oxLDL is that both modified LDLs involve the covalent attachment of short-chain substituents to the amino groups of lysine residues in apoprotein B (and possibly to other portions of the apoprotein B molecule) (Steinberg, D., et al., supra.). In view of the similarities between acLDL and oxLDL, it is not surprising that Stanton hypothesizes that internalization of oxidized LDL by macrophages contributes to foam cell formation in vivo (Stanton, L., et al., *J. Biol. Chem.* 267(31):22446–22451 (1992). Additional chemical and/or oxidative modifications which render the LDL lipoproteins capable of binding to the acLDL receptor by altering the lysine residues of apoprotein B include acetoacetylation, maleylation, succinylation and oxidative treatment of LDL such as that in malordialdehyde modified LDL (see U.S. Pat. No. 5,084,441 and references patents cited therein, the contents of which patents and references are incorporated herein by reference). Accordingly, it is believed that other modifications of the apoprotein B epsilon amino groups also will result in a modified LDL capable of inducing foam cell formation in vitro.

It is believed that binding of a stimulating ligand to the precursor receptor triggers secondary cellular events which lead to generation of the foam cell. Thus, to determine whether a "test" ligand is, indeed, a stimulating ligand for foam cell generation, two assays are performed: (1) an assay to determine whether the "test" ligand specifically binds to a receptor on the foam cell precursor and (2) an assay to determine whether the specifically bound "test" ligand induces uptake by the cell of lipid or lipoprotein (i.e., whether a form cell has been formed). In general, the specific binding of a stimulating ligand to a receptor is determined by incubating the receptor-containing cell (e.g., macrophage) in a medium containing labeled (e.g. radiolabeled) ligand and observing whether the ligand specifically binds to cell receptors. The determination of whether the test stimulating ligand induces foam cell formation in vitro is determined empirically by substituting the "test" ligand for a ligand known to induce foam cell formation (e.g., acLDL), contacting the test ligand with a macrophage under conditions known to induce foam cell formation in vitro and observing the occurrence (or lack thereof) of an increase in lipid or lipoprotein uptake. For example, lipoprotein and or cholesterol uptake by cells (as described in Roma et al. supra. and in the Examples) is one method for determining the existence of foam cell formation following contacting a foam cell precursor with a foam cell stimulating ligand.

Complexes of LDLs with other macromolecules, such as glycated-LDL complexes and fibronectin-LDL complexes, have been proposed as foam cell stimulating agents (Steinberg, D., et al., supra.). However, the precise mechanism by which these complexes facilitate foam cell generation has not been elucidated. Glycated- LDL is formed by exposing LDL to high concentrations of glucose for extended periods of time. The glycated-LDL is rapidly taken up by macrophages despite being less well recognized by the LDL receptor. Interestingly, glycation of autologous LDL in vivo renders it immunogenic and autoantibodies against glycated LDL have been demonstrated (See Steinberg, D., et al. *NEJM* 320(14):915–924 (1992)). Accordingly, it is believed that glycated-LDL and proteoglycan-LDL complexes may be taken up by the macrophage by way of the Fc receptor. To determine whether the binding of glycated-LDL to the Fc receptor triggers formation of a foam cell in vitro, one skilled in the art would assay the glycated-LDL for its ability to facilitate lipid or lipoprotein uptake as, for example, described in the Examples.

Similarly, Brown et al., report that complexes of LDL with antibodies against it ("immunoglobulin-LDL complexes") are incorporated by the macrophage (Brown, M. S. and Goldstein, J. L. *Annu. Rev. Biochem.* 52:223–261 (1983)). This uptake reportedly is mediated by the Fc receptor. More recently, Stanton et al., disclosed that a mouse receptor ("FcgammaRII-B2"), known to mediate immune complex uptake via recognition of the Fc region of IgG, is an additional high affinity receptor for oxLDL. Thus, disorders in which autoantibodies against a modified LDL are generated may favor foam cell formation in vivo. (Stanton, L., et al. supra.). Accordingly, an additional method for forming foam cells in vitro is by contacting a macrophage with an immunoglobulin-LDL complex, thereby triggering incorporation of the LDL via the Fc receptor.

In addition to receptors which internalize LDL by initially recognizing and binding to modified LDL or to the Fc portion of an antibody associated with LDL, it has also been reported that macrophages internalize beta-VLDL at a rate sufficient to generate foam cells and suggest that yet another macrophage receptor is involved in foam cell generation. (See Steinberg, D., et al., supra. and references cited therein.) The same gene that encodes the LDL receptor also reportedly encodes beta-VLDL receptor (Koo, C., et al., *J. Biol. Chem.* 261:11194–11201)). Thus, it appears that modified LDLs do not represent an exclusive class of compounds capable of inducing foam cell generation in vitro. (Steinberg, D., et al., supra.). There have also been reports in the literature that aggregates of LDL may be internalized by a lipoprotein receptor; however, these reports have not implicated LDL aggregates in the formation of foam cells in vivo.

The clinically relevant agent for delivery to the mammalian recipient may be virtually any compound, but preferably is a lipophilic compound or is associated with a lipophilic carrier. As used herein, the term agent embraces both therapeutic drugs and diagnostic agents. The term diagnostic reagent refers to an agent useful for visualizing or otherwise assessing the extent of the recipient's clinical condition. In a preferred embodiment, the agent is a therapeutic drug for preventing or treating a medical condition of the mammalian recipient.

As discussed below, one advantage of the instant invention as a vehicle for drug delivery is the ability of the drug-laden foam cell to minimize the degradation of drug that occurs when a drug is directly administered to a patient. Moreover, the foam cell containing the drug can be injected directly into lymph nodes. Accordingly, the instant invention offers advantages by allowing the direct injection of the foam cell drug carrier into the lymph node of the patient, thereby permitting the localized delivery of chemotherapeutic agents to the lymphatic system for the treatment of metastatic cancers which drain into the lymphatic system, e.g., cancers of the breast and malignant melanoma.

The foam cells of the instant invention can also be injected directly into tissue adjacent to that which has been removed by lumpectomy, thereby permitting the targetting of, for example, chemotherapeutic agents into this region.

Further, the foam cells of the instant invention can be injected through the cervical os (e.g., with a 22 guage canula) and into the uterine cavity. In this manner, foam cells containing agents for treating conditions such as endometriosis are adminstered to produce an atrophic endometrium. Such agents include norethindrone and other (androgenic) progestins.

It is believed that virtually any drug, but particularly any lipophilic drug, will be incorporated into the foam cell if present in the environment as the macrophage is converted into the foam cell (provided that the drug is not present in sufficient concentrations and/or for a sufficient period of time to exhibit a cytotoxic effect on the foam cell prior to its administration). Exemplary lipophilic compounds for which intestinal lymphatic transport has previously been demonstrated include cyclosporin, naftifine, probucol, various vitamin esters and derivatives, some hypolipidemic agents, xenobiotics, benzopyrene and polychlorinated biphenyls (PCBs) (see, e.g., Charman, W. and Stella, W., "Lymphatic Transport of Drugs", CRC Press, 1992, page 115, and references cited therein). Lipophilic agents such as stearols, including steroids, also can be incorporated into the foam cells. Additional lipophilic compounds useful as therapeutic agents will be readily apparent to one of ordinary skill in the art.

Non-lipophillic agents also can be incorporated into the foam cell by associating the agent with a lipophilic carrier prior to contacting the agent with the foam cell. According to one embodiment, the lipophilic carrier is an emulsion and the agent is suspended within the emulsion. Acceptable emulsion formulations for suspending the agent are known to one of ordinary skill in the art.

According to yet another embodiment, the lipophilic carrier is a liposome and the agent is suspended within the liposome. Methods for the preparation of liposomes containing lypophilic or non-lipophilic agents, are known to those of ordinary skill in the art.

In a preferred embodiment, the lipophilic carrier is covalently attached to a hydrophilic agent via a hydrolyzable bond to form a lipophilic prodrug. The preferred lipophilic carriers for prodrug formation include cholesterol, fatty acids and especially the naturally occurring fatty acids, glycerides, or combinations thereof. See e.g., Charman, W. and Stella, V., "Lymphatic Transport of Drugs," CRC Press, Boca Raton, Fla. (1992).

It will be understood that the active moiety of drugs, including toxic drugs, can be masked by conjugation with a carrier or by incorporation into liposomes. Such masking can permit incorporation of drugs into foam cells where otherwise it might not have been possible.

In yet another preferred embodiment, the agent is partitioned into the hydrophobic domain of a partitioning agent, such as a lipoprotein. If the agent is hydrophilic, it must first be derivatized with a lipophilic carrier before incorporation into the partitioning agent. For example, a hydrophilic agent can be chemically modified with a hydrophobic group (such as an ester- or amide-linked fatty acid, cholesterol or phospholipid) prior to contacting the agent with the partitioning agent. Lipophilic agents (e.g., cyclosporin) are partitioned into the lipoprotein without requiring covalent modification since the agent itself is of sufficient lipophilicity for partitioning into the hydrophobic domain of the partitioning agent. The preferred partitioning agent is acetyl-LDL. The formation of exemplary complexes using the preferred partitioning agent are described in U.S. Pat. No. 5,084,441, the contents of which patent are incorporated herein by reference.

The foam cells of the instant invention permit the delivery of a non-lipophilic drug to the mammalian recipient (e.g., via the lymphatic system) and further, permit sustained release of the drug from a biodegradable carrier (i.e., the foam cell). Thus, hydrophilic drugs which are presently difficult or impossible to deliver to a macrophage or to a target tissue (for example, due to enzymatic degradation of the drug upon administration to the patient or due to the drug's toxicity), are delivered to these targets by masking the drugs' hydrophilic nature. Although a drug delivery system for delivering nucleotide triphosphates (e.g., ddCTP) to cells of the monocyte-macrophage lineage has recently been reported (Magnani, M., et al., *PNAS USA* 89:6477–6481 (1992)), that system was directed to delivering the drug to macrophages in vivo. In contrast, the instant invention is directed to a drug delivery system in which the drug is introduced into a foam cell ex vivo and the foam cell is administered to the patient for delivering the drug in vivo following its release from the foam cell.

Classes of drugs which are intended to be included within this invention include neurotransmitters, anti-aids substances, anti-cancer substances, antibiotics, enzyme inhibitors, excitatory amino acids, histaminergics, ion channel modulators, muscle relaxants, agents, anti-hypertensives, analgesics, anti-pyretics and anti-inflammatory agents, local anesthetics, anti-spasmodics and muscle contractants, prostaglandins, anti-bacterials, anti-septics, central nervous system stimulants, imaging agents, specific targeting agents, proteins, peptides, anti-viral agents, anti-psychotic agents, anti-addiction agents and anti-emetics.

Neurotransmitters are substances which are released from a neuron on excitation and travel to either inhibit or excite a target cell. Examples of neurotransmitters include dopamine, serotonin, γ-aminobutyric acid, norepinephrine, histamine, acetylcholine, and epinephrine.

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine acyclovir (acyclovir), phosphonoformic acid, 1-adamantanamine, peptide T, 2',3' dideoxycytidine (ddC), and dideoxyinosine (ddI). Recently Fauci et al. (NEJM) have shown that the apparent long-term viral latency of HIV in seropositive patients may be an illusion and that this so-called viral latency is actually a period of clinical latency during which time virion particles reside in the tissue of the lymph system (particularly the nodes) persistently decimating this system despite the obvious humoral response detectable by assay. At such time as the lymph system begins to lose its viability, the disease of AIDS begins to become clinically manifest. It has been shown in other studies that treatment of seropositive patients that are clinically asymptomatic, with AZT and the other reverse transcriptase inhibitors during the asymptomatic period does not seem to improve survival and only exposes the patient to the considerable untoward side effects of the drugs which are systemically administered. Given this new paradigm of pathogenesis, a means of treating the seropositive, asymptomatic patient by the direct sustained release introduction of reverse transcriptase inhibitors into the lymph nodes and thus throughout the lymphatic tissue is reasonable. Thus, the anti-viral agents which target the virus (including, for example, antisense agents and inhibitors of reverse transcriptase) are internalized into the foam cells of the instant invention and delivered directly to the lymph nodes.

Sustained release of the agent(s) for treating the AIDs virus (or other disease or condition) is obtained by co-incorporating a therapeutic agent (or other agent) with a cytotoxic drug in the foam cell. The cytotoxic drug is internalized into the foam cell in accordance with any of the methods described herein for insertion of an agent into a macrophage. Thus, for example, a non-lipophilic cytotoxic drug can be derivatized with a lipophilic carrier, such that the toxic effect of the cytotoxic drug is masked. In such a manner, the foam cell (or foam cell precursor) is not exposed to the cytotoxic drug in vitro. Rather, the cytotoxic effect on the macrophage is released following metabolic conversion of the cytotoxic prodrug (or cytotoxic-lipid complex) to the cytotoxic drug in vivo. By preparing foam cells containing increasing amounts of the cytotoxic drug (along with, for example, a therapeutic agent), a method for the controlled release of the agent is attained. Thus, those cells including a high concentration of cytotoxic agent result in early foam cell death and the concommitant early release of therapeutic agent into the foam cell environment in vivo. Conversely, those cells including a low concentration of cytotoxic agent survive relatively longer and therefore release the therapeutic agent into the foam cell environment later.

Anti-cancer substances are substances used to treat or prevent cancer. Examples of such substances include chlorambucil, methotrexate, cisplatin, prednisone, hydroxyprogesterone caproate, medroxyprogesterone acetate, megestrol acetate, diethylstilbestrol, ethinyl estradiol, tamoxifen, testosterone propionate, fluoxymesterone, vinblastine (VLB), vincristine, vindesine, etoposide, teniposide, dactinomycin (actinomycin D), daunorubicin (daunomycin; rubidomycin), doxorubicin, bleomycin, plicamycin (mithramycin), mitomycin (mitomycin C), asparaginase, hydroxyurea, procarbazine (N-methylhydrazine, MIH), mitotane, aminoglutethimide, mechlorethamine, cyclophosphamide, melphalan (-sarcolysin), uracil mustard, chlorambucil, busulfan, carmustine (BCNU), lomusline (CCNU), semustine (methyl-CCNU), streptuzocin (steptozotocin), dacarbazine (DTIC: dimethyltriazenomidazolecarboxamide), methotrexate (amethopterin), fluorouracil (5-fluorouracil: 5-FU), cytarabine (cytosine arabinoxide), mercaptopurine (6-mercaptopurine: 6-MP), thioguanine (6-thioguanine: TG). Chlorambucil is an effective agent for the treatment of lymphomas. This agent contains a carboxylic acid functional group, making it amenable to chemical modification, e.g. as a glyceride. Garzon-Aburbeh et al., prepared 1,3-palmitoyl-2-[4-(bis(2-chloroethyl)amino]benzenebutan oyl]-glycerol which is a glyceride derivative of chlorambucil with the parent compound occupying the 2-position, and palmitic acid the 1- and 3- positions of the "triglyceride" (Garzon-Aburbeh, A., et al., *J. Med. Chem.* 26:1200 (1983) and see Charman, W. and Stella, V., "Lymphatic Transport of Drugs," CRC Press, p. 193 (1992)). The above-described chlorambucil prodrug can be internalized by the foam cell directly or, as described in the Examples, can be associated with a lipophilic carrier (e.g., suspended in an emulsion or partitioned within a lipophilic partitioning agent) prior to contacting the prodrug with the foam cell (or foam cell precursor).

Antibiotics are art recognized and are substances which inhibit the growth of or kill microorganisms. Antibiotics can be produced synthetically or by microorganisms. Examples of antibiotics include penicillin, tetracycline, minocycline, doxycycline, vanomycin, bacitracin, kanamycin, neomycin, erythromycin and cephalosporins. Examples of cephalosporins include cephalothin (keflin, seffin), cephapirin (cefadyl), cefazolin (ancef, kefzol), cephalexin (keflex), cephradine (anspor, velosef), cefadroxil (duricef, ultracef), cefamandole (mandol), cefoxitin (mefoxin), cefaclor (ceclor), cefuroxime (zinacef), cefonicid (monocid), ceforanide (precef), cefotaxime (claforan), moxalactam (moxam), ceftizoxime (cefizox), ceftriaxone (rocephin), and cefoperazone (cefobid).

Enzyme inhibitors are substances which inhibit an enzymatic reaction. Examples of enzyme inhibitors include edrophonium chloride, N-methylphysostigmine,(—)-, neostigmine bromide, physostigmine sulfate, tacrine HCL (THA), tacrine,1-hydroxy maleate, iodotubercidin, p-bromotetramisole,(—)-, 10-($\alpha$-diethylaminopropionyl)-phenothiazine hydrochloride (As-1397), calmidazolium chloride, hemicholinium-3, 3,5-dinitrocatechol (OR-486), diacylglycerol kinase inhibitor I (R59022), diacylglycerol kinase inhibitor II (R59949), 3-phenylpropargylamine, $N^6$-monomethyl-L-arginine acetate, carbidopa, 3-hydroxybenzylhydrazine HCl (NSD-1015), hydralazine HCl (apresoline), clorgyline HCl, deprenyl HCl,L(—)-, deprenyl HCl,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacin, 2-cyclooctyl-2-hydroxyethylamine hydrochloride (CONH), ($\pm$)-2,3-dichloro-$\alpha$-methylbenzylamine (DCMB),(LY-78335), 8,9-dichloro-2,3,4,5-tetrahydro-1H-2-benzazepine hydrochloride, p-aminoglutethimide,($\pm$)-, p-aminoglutethimide tartrate,R(+)-, p-aminoglutethimide tartrate,S(—)-, 3-iodotyrosine,L-, $\alpha$-methyltyrosine,L-, $\alpha$-methyltyrosine,D L-, and allopurinol.

Excitatory amino acids are amino acids used to activate or excite neurons involved in the glutaminergic or aspartic acid stimulated pathways. Excitatory amino acids include both agonists and antagonists. Excitatory amino acid agonists include (R,S)-$\alpha$-amino-3-hydroxy-5-methylisoxazole-4-propionic acid hydrobromide, (R,S)-$\alpha$-amino-3-hydroxy-5-methylisoxazole-4-propionic acid, aspartic acid,L-, glutamic acid HCl,L-, glutamic acid diethyl ester HCl,L-, ibotenic acid, kainic acid, N-methyl-D-aspartic acid (NMDA), cis-piperidine-2,3-dicarboxylic acid, and quisqualic acid,(+)-.

Excitatory amino acid antagonists include 3-amino-1-hydroxy-2-pyrrolidone (HA-966), 7-chlorokynurenic acid, 6-cyano-7-nitroquinoxaline-2,3-dione, dextromethorphan HBr, dextrorphan, 6,7-dinitroquinoxaline-2,3-dione, 5-fluoroindole-2-carboxylic acid, kynurenic acid, 2-amino-3-phosphonopropionic acid (AP-3), ($\pm$)-2-amino-4-phosphonobutyric acid (AP-4), 2-amino-5-phosphonopentanoic acid (AP-5), ($\pm$)-2-amino-7-phosphonoheptanoic acid (AP-7), ($\pm$)-3-(2-carboxypiperazin-4-yl)-propyl-1-phosphonic acid, ketamine HCl, (+)-5-methyl-10,11-dihydro-5H-dibenzo[a,d]cyclohepten-5,10-imine hydrogen maleate, (—)-5-methyl-10,11-dihydro-5H-dibenzo[a,d]cyclohep-ten-5, 10-iminehydrogen maleate.

Histaminergics are substances which interact or interfere in some manner with histamine and/or histamine receptors. Histaminergics include both histamine agonists and histamine antagonists. Histamine agonists include dimaprit, histamine HCl, histamine,$\alpha$-methyl oxalate,R(—)-. Histamine antagonists include cimetidine, chlorpheniramine maleate,($\pm$)-, chlorpheniramine maleate,(+)-, cyproheptadine HCl, ranitidine HCl, pyrilamine maleate. Other histaminergics include histidine HCl,L-, and histidine HCl,D-.

Ion channel modulators are compounds that modify the activity of receptors controlling the flow of ions into cells. Ion channel modulators include both ion channel activators and ion channel antagonists. An example of an ion channel activator includes 1,4-dihydro-2,6-dimethyl-5-nitro-4-[2-(trifluoromethyl)phenyl]-3-pyridinecarboxylic acidmethyl ester. Examples of ion channel antagonists include amiloride HCl, amiloride,5-(N,N-dimethyl)HCl, amiloride,5-(N,N-hexamethylene)-, amiodarone HCl, benzamil HCl, bepridil HCl, clofilium tosylate, $\omega$-conotoxin GVIA, cyproheptadine HCl, diltiazem HCl, R(+)-[(2-n-butyl-6,7-dichloro-2-cyclopentyl-2,3-dihydro-1-oxo-1H-inden-7-yl),oxy]acetic acid, flunarizine HCl, fluspirilene, R(+)-[(6,7-dichloro-2-cyclopentyl-2,3-dihydro-2-methyl-1-oxo-1H-inden-5-Yl)-ox y]acetic acid, lidocaine N-ethyl iodide, methoxyverapamil HCl,($\pm$)-, methoxyverapamil HCl,S(—)-, methoxyverapamil HCl,R(+)-, nifedipine, pimozide, ryanodine, 8-(diethylamino)octyl-3,4,5-trimethoxybenzoate hydrochloride, verapamil HCl,($\pm$)-, verapamil HCl,S(—)-, verapamil HCl,R(+)-. Other ion channel modulators include calmidazolium chloride, fluphenazine N-mustard, phenoxybenzamine HCl, trifluoperazine HCl, N-(6-aminohexyl)-5-chloro-1-naphthalenesulfonamide hydrochloride, N-(4-aminobutyl)-5-chloro-2-naphthalenesulfonamide hydrochloride, D(+)-myo-inositol-1,4,5-triphosphate (synthetic), N-(2-guanidinoethyl)-5-isoquinolinesulfonamide hydrochloride, 1-(5-isoquinolinesulfonyl)-2-methylpiperazine kihydrochloride, N-[2-(methylamino)ethyl]-5-isoquinolinesulfonamide dihydrochloride, N-(2-aminoethyl)-5-isoquinolinesulfonamide dihydrochloride, diacylglycerol kinase inhibitor I (R59022), diacylglycerol kinase inhibitor II (R59949), and N-(n-heptyl)-5-chloro-1-naphthalenesulfonamide.

Muscle relaxants and anti-parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Antihypertensives are substances capable of counteracting high blood pressure. Examples of such substances include $\alpha$-methyldapa, the pivaloyloxyethyl ester of $\alpha$-methyldapa and captopril.

Analgesics are substances capable of preventing, reducing, or relieving pain. Examples of analgesics include morphine sulfate, codeine sulfate, meperidine, and nalorphine.

Antipyretics are substances capable of relieving or reducing fever and anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which have an anesthetic effect in a localized region. Examples of such anesthetics include procaine, lidocaine, tetracaine and dibucaine.

Antispasmodics and muscle contractants are substances capable of preventing or relieving muscle spasms or contractions. Examples of such agents include atropine, scopolamine, oxyphenonium, and papaverine.

Prostaglandins are art recognized and are a class of naturally occurring chemically related, long-chain hydroxy fatty acids that have a variety of biological effects. Examples of such agents include E2, and E1.

Anti-bacterials are substances which destroy or suppress the growth or reproduction of bacteria. Examples of anti-bacterials include trimethoprin, sulfamethoxazole, cefoperazone, chloroamphenicol, polymycin, and metronidazole.

Antiseptics are substances capable of inhibiting the growth and development of microorganisms without necessarily destroying them. Examples of antiseptics include those discussed above as anti-bacterials and other sulfonamide substances.

Central nervous system stimulants are substances capable of stimulating the central nervous system. Examples of such substances include amphetamine, phenylalanine, picrotoxinin, and methylphenidate.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a drug.

As is apparent from the foregoing discussion, the agent for delivery to the mammalian recipient can take a variety of forms, e.g., as an emulsion containing the agent, as a prodrug including the agent coupled to a hydrophobic carrier, or as an agent partitioned into a lipophilic carrier. Thus, to practice the method of the instant invention, foam cells are contacted with agents that are in soluble (e.g., emulsion) or insoluble form (e.g., agents coupled to or partitioned in a lipophilic carrier such as LDL or acLDL). Insoluble forms of agent can be coated onto a substrate (e.g., a tissue culture dish, membrane, or mesh) such that the substrate also contains the foam cell precursor. In this manner, contacting the precursor with the agent occurs concurrently with foam cell generation. For example, macrophages can be cultured in a tissue culture plate having a bottom surface that is coated with an agent-LDL prodrug. Upon incubating the macrophage with the appropriate foam cell stimulating ligand, the macrophage is transformed into a foam cell which then internalizes the insoluble agent-LDL prodrug. Insoluble forms of agent (e.g., agent coupled to LDL or modified LDL) can be coated onto a substrate by, for example, melting the insoluble modified LDL, pouring it into a culture plate and permitting the plate to cool, thereby resulting in recrystallization of the melted modified LDL containing the agent. Other methods of coating an insoluble lipid onto a surface will be readily apparent to one of ordinary skill in the art.

The foam cells containing the agent are administered to the mammalian recipient according to any appropriate mode of administration known in the art, e.g., injection into the blood stream or the lymphatic system of the individual. Preferably, the foam cells are administered by injecting the foam cells directly into a lymph node. In a preferred embodiment, the foam cell is administered to the mammalian recipient in the presence of oxidized LDL. Oxidized LDL is reported to limit foam cell mobility (see Steinberg, D., et al., *NEJM* 320(14):915–923 (1989) and references cited therein). Accordingly, it is believed that the administration of foam cells in the presence of oxLDL will extend the time period during which the foam cell is present at the site of injection.

The invention also provides a method for making a pharmaceutical preparation for administration to a mammalian recipient. The isolated foam cell precursors are treated extracorporeally to form a foam cell precursor having enhanced expression of the stimulating receptors in comparison with foam cell precursors which have not been so treated. The treated foam cell precursors (having enhanced expression of the receptor) are reacted with foam cell stimulating ligands (specific for that receptor) extracorporeally to form foam cells. Preferably, the foam cells are reacted with an excess of the stimulating ligands to ensure that each receptor is bound to a stimulating ligand. More preferably, the foam cell is reacted with stimulating ligand in the presence of the agent (e.g., a therapeutic drug) intended for delivery to the mammalian recipient.

Also within the scope of the invention are pharmaceutical compositions comprising a pharmaceutically acceptable carrier and a plurality of foam cells containing the agent. The plurality of foam cells differs from the corresponding naturally occurring foam cells in several respects: (1) the foam cells have an elevated concentration of receptor molecules on a per cell basis and (2) in a preferred embodiment, these receptors are saturated with a corresponding stimulating ligand.

EXAMPLES

Isolation of Human Monocyte-Derived Macrophages: (a) Isolation of Mononuclear Cells.

Mononuclear cells are isolated according to the method of Magnani, et al., *PNAS USA* 89:6477–6481 (1992). Briefly, mononuclear cells are prepared by Ficoll-Paque sedimentation from leukapheresesd donors, washed twice in sterile saline, and cultured in RPMI medium supplemented with 20% (vol/vol) heat inactivated human serum. Nonadherent cells are removed and the monocyte/macrophage ("M/M") cells are maintained in RPMI medium supplemented with 10% (vol/vol) fetal calf serum. The proportion of M/M cells is determined by nonspecific esterase staining, Leu-M3positivity and/or acLDL receptor quantitation according to methods known to one of ordinary skill in the art.

Alternatively, monocytes are isolated from whole blood by cytopheresis and cultured with autologous serum as reported in Andreesen, R., *Cancer Detect. Prev.* 15(5):413–421 (1991).

(b) Differentiation of Monocytes into Macrophages.

Prior to harvesting the above-described cells, recombinant human interferon gamma is added at approximately 200 IU/ml to induce differentiation of the monocytes into macrophages (Andreesen, R., et al., supra.).

(c) Cell Viability.

Cell viability is determined according to Roma, R., et al., supra. Cells are incubated in MEM (Gibco, Madison, Wis.) +0.2% FAF-BSA (fatty acid-free bovine serum albumin) ("medium A") alone or with OxLDL or AcLDL (50 ug lipoprotein cholesterol/ml). At different times, washed cells are gently scraped with a Teflon policeman, pelleted by centrifugation (80 g), and resuspended in Trypan Blue diluted 1:10 with saline. Dye-permeable versus -impermeable cells are counted under a microscope in a Neubauer chamber; a minimum of 100 cells per experiment are counted.

The release of lactate dehydrogenase (LDH) into the culture medium (as an indicator of cell viability) is quantitated by spectrophotometric measurement of NADH consumption over time, using a commercially available kit (merck LDH, Merck, Darmstadt, Germany). Enzyme activity is expressed at U/1.

2. Lipoproteins:

(a) Source of LDL.

LDL is a commercially available preparation (Bionetics Research Institute, Rockville, Md.) or is prepared according to Roma, R., et al., supra. as described herein. LDL (d 1.019–1.063 g/ml) is isolated from freshly isolated human plasma containing 0.01% EDTA (w/v) and 0.01% $NaN_3$ (w/v) by sequential ultracentrifugation (Havel, R. J., *J. Clin. Invest.* 34:1345–1353 (1955)) at 4° C. and 40,000 rpm in a 60 Ti rotor, using a L5-50 ultracentrifuge (Beckman, Palo Alto, Calif.).

(b) Acetylation of LDL

Acetylation of LDL is performed according to the method of Roma, P., et al., supra. LDL is extensively dialyzed against 0.15 M NaCl, pH 7.4, diluted with an equal volume of saturated Na acetate and treated with acetic anhydride, according to Basu et al. (Basu, S. K., et al., *Proc. Natl. Acad. Sci. USA* 73:3178–3182)).

(c) Oxidation of LDL

For oxidation, LDL is desalted by gel filtration on Sephadex G-25 columns (PD-10, Pharmacia Fine Chemicals, Uppsala, Sweden) eluted with PBS, pH 7.4. Chemical oxidation is performed under sterile conditions, by incubating LDL at 37° C. for 24 h, at 0.2 mg protein/ml in PBS+20 M $CuSO_4$. Oxidation is blocked in ice, with the addition of BHT (final concentration 40 M) dissolved in ethanol to the incubation mixture.

Biological oxidation is obtained, under sterile conditions, by incubating LDL in the presence of EAhy-926 cells at 37° C. for 24 h, at a concentration of 0.07–0.1 mg protein/ml, in serum-free medium containing 12 M $CuSo_4$ (20); since HAT acts as an antioxidant, lower concentrations of $CuSO_4$ cannot be used. Oxidation is blocked as above. LDL incubated in the same conditions, but in the absence of cells, are used as control lipoproteins for BioOxLDL.

Modification of LDL with the products of fatty acid oxidation (LinOxLDL) is performed according to Steinbrecher et al (Steinbrecher, U. P., et al., *J. Biol. Chem.* 264:15216–15223)). Briefly, linolenic acid (85 ul, equivalent to 85 ug) is incubated at 100° C. for 1 h and subsequently extracted with 100 volumes of $CHCl_3$-PBS 1:1 (v/v). The aqueous phase is collected and incubated at room temperature for 18–20 h with 1.0 mg LDL at a final concentration of 0.2 mg/ml. Antiproteolytic agents (PMSF 1 mM, aprotinin 0.5 g/ml, and phenantrolin 1 mM) are added to the incubation.

Oxidized LDL and LinOxLDL are concentrated by ultrafiltration under $N_2$ pressure on Diaflo Ultrafiltration Membranes YM 100 (American Corporation, Lexington, Mass.), desalted on Sephadex G-25 columns eluted with PBS, and sterile-filtered. Modifications of lipoproteins are tested by nondenaturing gel electrophoresis in 0.8% agarose (Agarose $A_r$-Pharmacia Fine Chemicals) in 0.1M Tris, pH 8.6, at 200 V (22). Gels were fixed in 70% ethanol, dried, and stained with Sudan Black in 70% ethanol.

(d) Iodination of Lipoproteins and detection reagents

Iodination of lipoproteins is performed as described in Roma, P., et al. supra. and the references described therein. Lipoproteins are labeled with 125I according to Bilheimer, Eisenberg, and Levy (Bilheimer, D. W., et al., *Biochim. Biophys. Acta.* 250:212–221 (1973)), desalted against PBS by gel filtration over Sephadex G-25 and sterile-filtered. Roma, et al., report that for unknown reasons, TCA-nonprecipitable radioactivity, usually about 2% of total for lipoproteins, was consistently higher (approximately 10%) in the case of OxLDL, and was reduced (approximately 3%) by extensive dialysis. Based upon the results reported by Roma, P., et al. supra., specific-activityin the range of about 200–300 cpm/ng lipoprotein protein is expected. Goat anti-mouse IgG (100 ug) is labeled with $^{125}I$ in the presence of Iodogen (100 ug) (Pierce, Oud-Beijerland, The Netherlands), according to a published procedure (Fraker, P. J. and Specker, Jr., J. C. *Biochem. Biophys. Res. Commun.* 80:849–857 (1980)). Based upon the results reported by Roma et al., TCA-nonprecipitable radioactivity is expected to be about 2% of total and specific activity is expected to be approximately 4,800 cpm/ng.

3. Preparation of Lipophilic Agent for Internalization by the Foam Cell (a) A Model Chemotherapeutic Agent Derivatization with a fatty acid to form a prodrug and suspension of the prodrug in an emulsion for delivery to a macrophage A fatty acid derivative of chlorambucil is prepared according to Garzon-Aberbeh, et al., *J. Med. Chem.* 26:1200 (1983). The resultant prodrug, 1,3-palmitoyl-2-[4-(bis(2-chloroethyl)amino]benzenebutanoyl]-glycerol, is a glyceride derivative of chlorambucil with the parent compound occupying the 2-position, and palmitic acid the 1- and 3-positions of the "triglyceride") (see e.g., Charman, W. and Stella, V., "Lymphatic Transport of Drugs", CRC Press (1992). The prodrug is suspended in an emulsion formulation according to methods known to one of ordinary skill in the art (Charman, W. and Stella, V., supra. and references cited therein, in particular, the references cited on pages 256 and 273–274 of the above-identified text). Thereafter, the foam cells (or foam cell precursors, e.g., macrophages, in the process of transformation to foam cells), are contacted with the emulsion (containing the prodrug) under conditions which facilitate uptake of the prodrug by the foam cell, e.g., the conditions described herein for cholesterol uptake by stimulated macrophages.

(b) A Model Chemotherapeutic Agent: Derivatization with a fatty acid to form a prodrug and partitioning of the prodrug in LDL or acLDL for delivery to a macrophage The above-described chlorambucil prodrug is partitioned into actyl LDL as disclosed in U.S. Pat. No. 5,084,441, the contents of which patent are incorporated herein by reference. Briefly, in a glass tube, methanol solubilized chlorambucil prodrug (a range of concentrations are tested to determine the optimum concentration for partitioning into acLDL) is evaporated to dryness with argon and acetyl-LDL (approximately 204 mg) is added in about 2–3 ml of PBS buffer. The mixture is stirred gently with a Teflon-coated stirring bar for 2 hours in the dark at about 37° C. to 40° C. under argon. Following incubation, the sample is loaded on a $1 \times 10$ cm column of Sephadex G15-120 and the acetyl-LDL:chlorambucil prodrug complex is collected. The complex is passed through a 0.45 $\mu$m Millex filter for removal of possible aggregated acetyl-LDL:chlorambucil prodrug and for sterilization. The chlorambucil prodrug concentration is determined after extraction of the complex from the acLDL according to methods known to one of ordinary skill in the art.

4. Formation of Foam Cells (a) Selecting a Foam Cell Stimulating Ligand Binding and internalization of "test" stimulating ligands In this experiment, two sets of conditions are used: a) foam cell precursors (e.g., macrophages) are incubated at 4° C. for 2 h in $HCO_3$-free medium A, 10 mM HEPES, containing $^{125}$I-labeled OxLDL (10 ug/ml); or b) cells are incubated at 37° C. for 5 h in medium A, containing the radioactive lipoproteins as above. Cells from a) and b) are washed and incubated in medium A at 37° C. for 10 min. with trypsin (0.05%) or pronase (0.25%), or at 4° C. for 1 h in the presence of an excess of unlabeled ligand (1 mg/ml). Radioactivity released into the medium by these treatments is attributed to the binding component of total uptake, whereas the remaining cell-associated radioactivity is attributed to internalization.

(b) Contacting the MaCrophage with the Selected foam cell stimulating agent to form a foam cell The incubation of macrophage with a selected foam cell stimulating ligand, e.g., acLDL, is performed as described above except that substantially higher concentrations (e.g., at least about 5-fold and preferably, at least about 10-fold) of unlabeled ligand is used instead of the relatively small amounts of radiolabeled ligand employed in the ligand selection protocol. The amount of ligand is selected so that it is present in the medium at a concentration in excess of the number of macrophage receptors for the ligand.

(c) Determining whether foam cells have been formed

The formation of foam cells in vitro is determined by exposing the presumed foam cells to lipoprotein and determining the uptake by the cell of the lipoprotein. This is most easily accomplished by determining the uptake of cholesterol by the cells, according to the method of Roma, P., et al., supra. Alternatively, the formation of foam cells is determined by scanning electron microscopy (SEM) and observing whether lipid-containing vesicles are present in the cell.

(d) Incorporation of Agent into a foam cell

Macrophages are incubated at 37° C. in medium A alone or containing modified lipoproteins or other "test" foam cell stimulating ligands at increasing concentrations for 18 h. The cells are optionally co-incubated in the presence of a lipoprotein containing agent, or are subsequently transferred to a culture vessel containing a lipoprotein containing agent. Preferably, the vessel contains an excess concentration of lipoprotein-containing agent, e.g., at least about a 5-fold excess and preferably, at least about a 10-fold excess of agent to macrophage. To assess whether the agent has been internalized, the cells are washed and the agent-associated lipids are extracted from washed cells by a 30-min. incubation at room temperature in hexane-isopropyl alcohol 3:2 (v/v), followed by a brief wash in the same mixture. Cellular proteins are dissolved in 1 N NaOH and quantitated according to Lowry et al. (Lowry, O. H., et al., J. Biol. Chem. 193:265–275 (1951)), using BSA as a standard. The combined lipid extracts are dried under a $N_2$ stream and redissolved in 200 ul of hexane; 70 ul of the extract is used for the determination of total cholesterol by an enzymatic colorimetric assay (Trinder, P. Ann. Clin. Blochem. 6:24–27 (1969)). The amount of agent present in the cell extracts is determined according to methods known in the art for quantitating the specific agent (e.g., immunoassays, enzyme assays). Alternatively or additionally, SEM is used to determine whether the lipid containing the agent has been internalized.

5. Administration of Foam Cells containing a Lipophilic Agent to a Patient

The foam cells containing the agent for delivery to the mammalian recipient are administered to the recipient according to methods known to one of ordinary skill in the art. Preferably the foam cells are delivered directly to the lymphatic system via regional introduction, such as subcutaneous injection for limbs and trunk, head, neck or by intraperitoneal injection. Alternatively, delivery is by intra-arterial or direct lymphatic or intraperitoneal or pleural injection to the lymph nodes, or via the thoracic duct.

It should be understood that the preceding is merely a detailed description of certain preferred embodiments. It therefore should be apparent to those skilled in the art that various modifications and equivalents can be made without departing from the spirit or scope of the invention.

What is claimed is:

1. A method for delivering a lipophilic agent to a mammalian recipient, the method comprising:
   (a) contacting an isolated foam cell precursor having a modified LDL receptor with a foam cell stimulating ligand in the presence of the lipophilic agent to form a foam cell containing the lipophilic agent; and
   (b) parenterally administering the foam cell containing the lipophilic agent to the mammaliam recipient,
   wherein the foam cell precursor is selected from the group consisting of a promonocyte, a monocyte, a macrophage and a smooth muscle cell and wherein the modified LCL receptor is selected from the group consisting of an acetyl LDL receptor, a receptor for LDL aggregates and an Fc receptor.

2. A method as claimed in claim 1, wherein the foam cell stimulating ligand comprises an agonist of the foam cell precursor modified LDL receptor.

3. A method as claimed in claim 1 wherein the foam cell stimulating ligand comprises a modified LDL selected from the group consisting of acetyl LDL, oxidized LDL propteoglycan-LDL complexes, fibronectin-LDL complexes, aggregates of LDL, glycated LDL and immunolobulin-LDL complexes.

4. A method as claimed in claim 3, wherein the modified LDL comprises oxidized LDL.

5. A method as claimed in claim 1, wherein the foam cell stimulating ligand comprises a beta-VLDL.

6. A method as claimed in claim 1, wherein the foam cell precursor is isolated from the mammalian recipient.

7. A method as claimed in claim 1, wherein the lipophilic agent is selected from the group consisting of cyclosporin, naftifine, probucol, vitamins, hypolipidemic agents, xenobiotics, benzopyrene and polychlorinated biphenyls.

8. A method as claimed in claim 1, wherein the lipophilic agent comprises a nonlipophilic agent attached to a lipophilic carrier to form a lipophilic prodrug.

9. A method as claimed in claim 8, wherein the lipophilic carrier is selected from the group consisting of a fatty acid, a glyceride or combinations thereof.

10. A method as claimed in claim 8, wherein the lipophilic prodrug comprises a chemotherapeutic agent.

11. A method as claimed in claim 10, wherein the chemotherapeutic agent is chlorambucil.

12. A method as claimed in claim 10, wherein the chemotherapeutic agent is for treating metastatic cancers which drain into the lymphatic system.

13. A method as claimed in claim 1, wherein parenterally administering the foam cell comprises injecting the foam cell into a lymph node.

14. A method as claimed in claim 13, wherein the foam cell is injected in the presence of oxidized LDL.

15. A method as claimed in claim 1, wherein parenterally administering the foam cell comprises injecting the foam cell through the cervical oss into the uterine cavity.

* * * * *